United States Patent
Carrion Villarnovo et al.

(10) Patent No.: US 10,070,653 B2
(45) Date of Patent: Sep. 11, 2018

(54) **USES, METHODS AND BIOLOGICAL COMPOSITIONS OF THE GENUS *PAECILOMYCES* IN THE CONTROL, PREVENTION AND ERADICATION OF PLANT PARASITES IN SOLANACEAE CULTURES**

(75) Inventors: Gloria Luz Laura Carrion Villarnovo, Veracruz (MX); Tania Isadora Hernandez Leal, Veracruz (MX); Jose Daniel Lopez Lima, Veracruz (MX); Angel Enrique Nunez Sanchez, Veracruz (MX)

(73) Assignee: Instituto de Ecologia, A.C., Veracruz (MX)

( * ) Notice: Subject to any disclaimer, the term of this patent is extended or adjusted under 35 U.S.C. 154(b) by 917 days.

(21) Appl. No.: 14/114,662

(22) PCT Filed: Mar. 28, 2012

(86) PCT No.: PCT/MX2012/000032
§ 371 (c)(1),
(2), (4) Date: Oct. 29, 2013

(87) PCT Pub. No.: WO2012/148251
PCT Pub. Date: Nov. 1, 2012

(65) Prior Publication Data
US 2014/0079670 A1    Mar. 20, 2014

(30) Foreign Application Priority Data
Apr. 29, 2011    (MX) .................... MX/a/2011/004510

(51) Int. Cl.
*A01N 63/00*    (2006.01)
*A01N 63/04*    (2006.01)
(Continued)

(52) U.S. Cl.
CPC .............. *A01N 63/04* (2013.01); *C12N 1/14* (2013.01); *C12R 1/79* (2013.01)

(58) Field of Classification Search
None
See application file for complete search history.

(56) References Cited

U.S. PATENT DOCUMENTS 4,751,082 A * 6/1988 Schaerffenberg ...... A01N 63/04
424/93.5
5,360,607 A    11/1994 Eyal et al.
(Continued)

FOREIGN PATENT DOCUMENTS

CA    2059642    2/1991
CN    101081982 A    12/2007
(Continued)

OTHER PUBLICATIONS

Nunez, A.E. Aislamieto y evaluacion de hongos nematofagos asociados a quistes de Globodera rostochiensis (Woll.) en la region del Cofre de Perote. Thesis, School Biological and Agricultural Science. Tecoman, Colima, University of Colima, Mexico. 107 pages. pp. 1, 50, 66, 75,78, 93.2002.*
(Continued)

*Primary Examiner* — Blaine Lankford
*Assistant Examiner* — Lauren K Van Buren
(74) *Attorney, Agent, or Firm* — The Webb Law Firm

(57) ABSTRACT

The invention relates to the method for producing the fungus *Paecilomyces* spp., and to the uses, methods and nematicide compositions for the prevention and/or control and/or eradication of nematodes that form cysts developing in solanaceae cultures. Said invention includes a system for the application of the fungus combined with the rotation of
(Continued)

Figure 1:
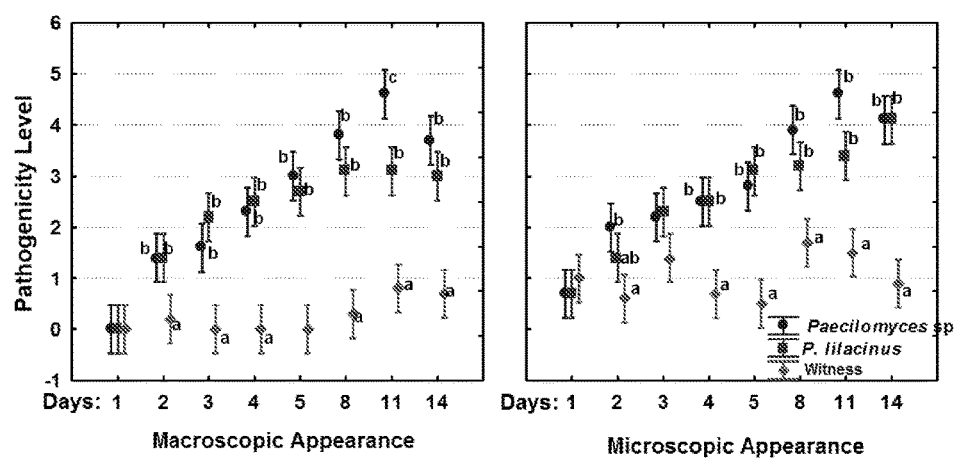
Figure 2:
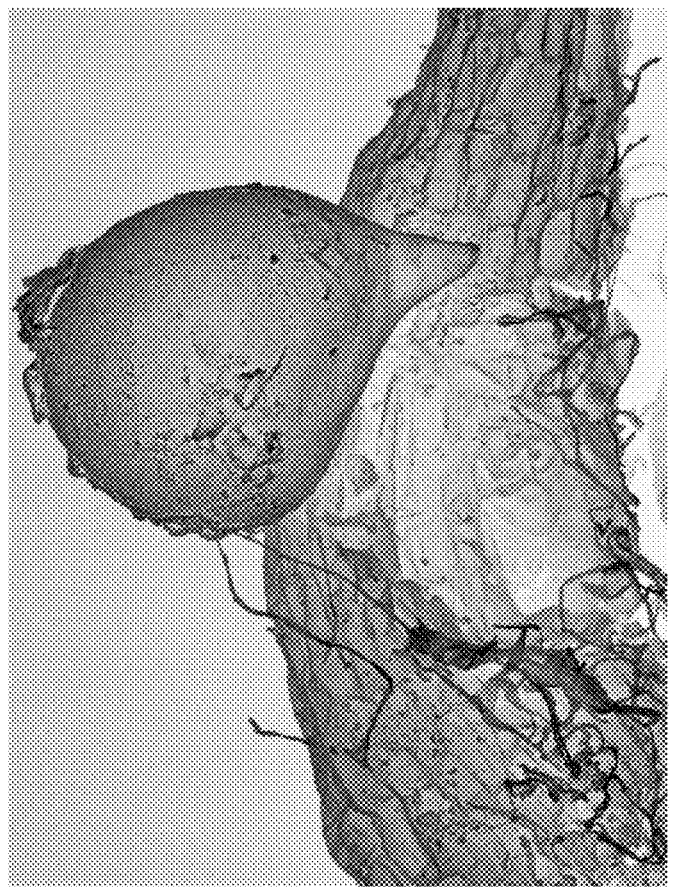
Figure 3:
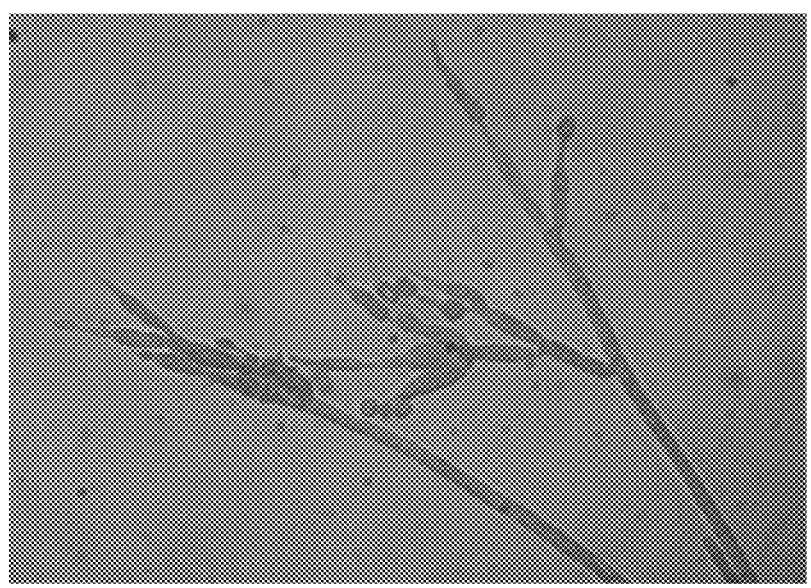
Figure 4:
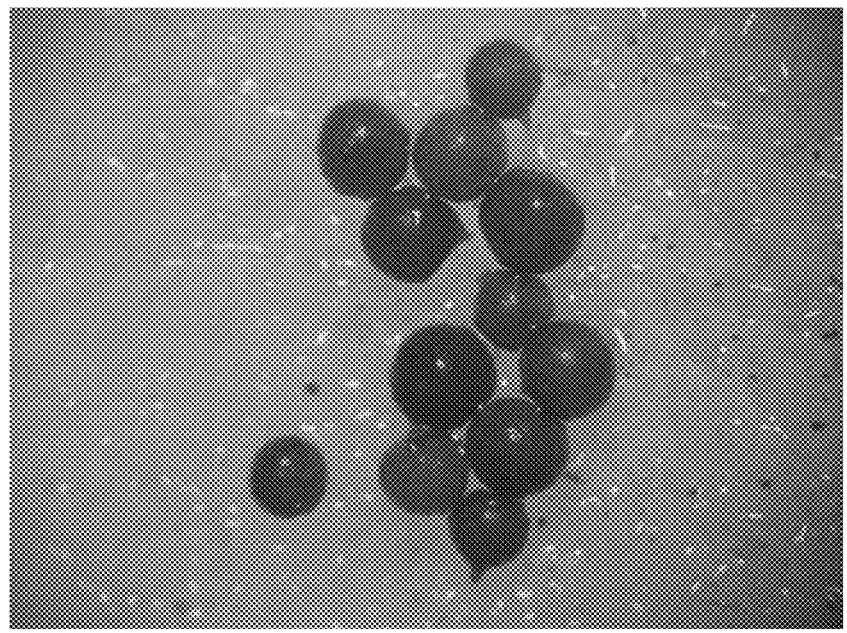
Figure 5:

cultures for effectively and efficiently reducing the viability of the cysts of nematodes in solanaceae cultures.

10 Claims, 3 Drawing Sheets

Specification includes a Sequence Listing.

(51) Int. Cl.

| | |
|---|---|
| *C12R 1/79* | (2006.01) |
| *C12N 1/14* | (2006.01) |

(56) References Cited

U.S. PATENT DOCUMENTS

| | | | |
|---|---|---|---|
| 5,989,543 | A | 11/1999 | Davidé et al. |
| 7,033,586 | B2 | 4/2006 | Shimizu et al. |
| 7,390,480 | B2 | 6/2008 | Wright et al. |
| 7,435,411 | B2 | 10/2008 | Park et al. |
| 2003/0124098 | A1 | 7/2003 | Shimizu et al. |
| 2005/0008619 | A1 | 1/2005 | Park et al. |
| 2007/0141032 | A1 | 6/2007 | Matsumura et al. |

FOREIGN PATENT DOCUMENTS

| | | | | |
|---|---|---|---|---|
| CN | 101273728 | A | | 10/2008 |
| CN | 101331880 | A | | 12/2008 |
| CN | 101331884 | A | | 12/2008 |
| CN | 101418264 | A | | 4/2009 |
| CN | 101422168 | A | | 5/2009 |
| CN | 101423799 | | * | 5/2009 |
| CN | 101502270 | A | | 8/2009 |
| CN | 101518265 | A | | 9/2009 |
| DE | 102005024783 | A1 | | 12/2006 |
| JP | 3190807 | A | | 8/1991 |
| KR | 20030094540 | A | | 12/2003 |
| WO | 9211856 | A1 | | 7/1992 |
| WO | 9215690 | A1 | | 9/1992 |
| WO | 9302083 | A1 | | 2/1993 |
| WO | 9319604 | A1 | | 10/1993 |
| WO | 9510187 | A1 | | 4/1995 |
| WO | 9959414 | A1 | | 11/1999 |
| WO | 0100841 | A1 | | 1/2001 |
| WO | 0194601 | A2 | | 12/2001 |
| WO | 2007132224 | A2 | | 11/2007 |
| WO | 2008087555 | A2 | | 7/2008 |

OTHER PUBLICATIONS

Nunez, A.E. Aislamieto y evaluacion de hongos nematofagos asociados a quistes de Globodera rostochiensis (Woll.) en al region del Cofre de Perote. Thesis, School Biological and Agricultural Science. Tecoman, Colima, University of Colima, Mexico. 107 pages. pp. 1, 50, 66, 75,78,93.2002.*

Translation of Portions of Nunez.*

Pestnet Query, date Feb. 2001, http://www.pestnet.org/SummariesofMessages/Pests/PestsEntities/Fungi/Culturetechniques,Paecilomyces,NewCaledonia.aspx.*

Nunez, A.E. Aislamieto y evaluacion de hongos nematofagos asociados a quises de Globodera rostochiensis (Woll.) en al region del Cofre de Perote. Thesis, School Biological and Agricultural Science. Tecoman, Colima, University of Colima, Mexico, 107 pages. pp. 1, 50,66,75,78,93,2002 with Translation.*

Norma Mexican Official Standard. NOM040-FITO-2002. 10 pages.

Nunez Sanchez. Aislamiento y evalución de hongos nematófagos asociados a quistes de Globodera rostochiensis (Woll.) en la región del cofre de Perote. 2002. Tesis Facultad de Ciencias Biologicas y Agropecuarias Tecoman, Colima, Universidad de Colima Mexico.

Ortega-Cartaya. El nematodo quiste de la papa. II. Gestión integrada de control y prospectiva de la restricción cuarentenaria para la producción y distribución de tubéculo-semilla en el Mundo. Revista Digital INIA HOY. Jan.-Apr. 2008. No. 1, pp. 1-12.

* cited by examiner

SEQUENCE LISTING

<160> NUMBER OF SEQ ID NOS: 2

<210> SEQ ID NO 1
<211> LENGTH: 520
<212> TYPE: DNA
<213> ORGANISM: Paecilomyces carneus

```
<400> SEQUENCE: 1
cccctgtgaa cttataccat ttactgttgc ttcggcgggt cacggccccg gggaaggaca        60
gcggtcgccg tcaggcctca gctgcccgcc cccggaaaca ggcgcccgcc ggggaactca       120
aactcttctg tatttcttta tctaatatat actgtctgag taaaaactaa aatgaatcaa       180
aactttcaac aacggatctc ttggttctgg catcgatgaa gaacgcagcg aaatgcgata       240
agtaatgtga attgcagaat tcagtgaatc atcgaatctt tgaacgcaca ttgcgcccgc       300
cagtattctg gcgggcatgc ctgttcgagc gtcatttcaa ccctcaagtc ccctgtggac       360
tcggtgttgg ggaccggcga gacagccgcg gatcttcttc cgcagcgagt cgccgccccc       420
caaatgactt ggcggcctcg tcgcggccct cctctgcgta gtatagcaca cctcgcaaca       480
ggagcccggc gaatggccac tgccgtaaaa cccccaact                              520

<210> SEQ ID NO 2
<211> LENGTH: 824
<212> TYPE: DNA
<213> ORGANISM: Paecilomyces carneus

<400> SEQUENCE: 2
tttgcagagg atgcttttgg caaggtgcct tccgagttcc ctggaacggg acgccataga        60
gggtgagagc cccgtctggt tggataccga gcctctgtaa agctccttcg acgagtcgag       120
tagtttggga atgctgctct aaatgggagg tatatgtctt ctaaagctaa atattggcca       180
gagaccgata gcgcacaagt agagtgatcg aaagatgaaa agcactttga aaagagggtt       240
aaatagtacg tgaaattgtt gaaagggaag cgctcatgac cagacttggg cccggtgaat       300
catccagcgc tcgtcgctgg tgcactttgc cgggctcagg ccagcatcag ttcgctccgg       360
gggacaaagg ctctgggaat gtggctcctc cgggagtgtt atagcccact gcgcaatacc       420
ctggggcgga ctgaggttcg cgcattcgtg caaggatgct ggcgtaatgg tcatcagtga       480
cccgtcttga aacacggacc aaggagtcgt cttcgtatgc aagtgttcgg gtgtaaaacc       540
cctacgcgta atgaaagtga acgcaggtga gagcttcggc gcatcatcga ccgatcctga       600
tgttctcgga tggatttgag taagagcata cggggccgga cccgaaagaa ggtgaactat       660
gcctgtatag ggtgaagcca gaggaaactc tggtggaggc tcgcagcggt tctgacgtgc       720
gcctgtatag ggtgaagcca gaggaaactc tggtggaggc tcgcagcggt tctgacgtgc       780
aaatcgatcg tcaaatatgg gcatgggggc gaaagactaa tcga                       824
```

USES, METHODS AND BIOLOGICAL COMPOSITIONS OF THE GENUS *PAECILOMYCES* IN THE CONTROL, PREVENTION AND ERADICATION OF PLANT PARASITES IN SOLANACEAE CULTURES

CROSS-REFERENCE TO RELATED APPLICATIONS

This application is the United States national phase of International Application No. PCT/MX2012/000032 filed Mar. 28, 2012, and claims priority to Mexican Patent Application No. MX/a/2011/004510 filed Apr. 29, 2011, the disclosures of which are hereby incorporated in their entirety by reference.

The Sequence Listing associated with this application is filed in electronic format via EFS-Web and is hereby incorporated by reference into the specification in its entirety. The name of the text file containing the Sequence Listing is 6229-133776-1_ST25.txt. The size of the text file is 2,645 bytes, and the text file was created on Feb. 25, 2014.

FIELD OF THE INVENTION

This invention relates to a method to obtain the fungus *Paecilomyces* spp. and further relates to the uses, methods and biological compositions functioning as nematicide for the prevention and/or control and/or eradication of cyst-forming nematodes growing onto Solanaceae cultures.

This invention includes a system to apply said fungus combined with crops rotation, so as to surprisingly decrease in an effective and efficient manner, never known in the state of the art, the viability of the nematode cysts highly harmful to the production of Solanaceae cultures, such as potato, tomato and eggplant, among other. This invention has the advantage of being innocuous both for the product, the soil, and the producer and end consumer, as it does not contribute in the obtainment of an organic product.

BACKGROUND OF THE INVENTION

Nematodes are generally multi-cellular filiform microscopic plant parasites, with reduced diameter ends. Generally, nematodes are dioic (there are males and females) and the reproduction thereof implies a crossed fecundation. As per their biologic cycle this has six stages: a cyst, four juvenile stages (J1, J2, J3 and J4) and adult. Cysts remain into the soil infecting the roots of cultures during the following culture cycle. A nematode may have up to six generations during a culture time depending on the date of seeding, the temperature of the soil, the length of the growing time, the type of host and the geographic zone. Cysts can remain viable for long periods of time of up to twenty years.

Generally, nematodes, upon infecting cultures, produce aerial damages, such as a reduction in the seeds germination, low production, foliar stains, decay and chlorosity, dwarfism, leaf and stem deformation, internal necrosis in stem, defoliation and lack of greenness and under earth damages such as nodulated roots, detaching and necrosis of the skin on roots, corms and tubercles, low production of seeds and buds or shoots, deformation and necrosis of roots, bulbs, tubercles and corns, excess proliferation of roots, atrophy of radical apexes or an underdeveloped radical system.

An infestation by *Globodera rostochiensis* (FIG. 2) is produced when larvae J2 burst under the stimuli from radicals exuded out from the plant. Said J2 enter the apical portion of the root, into the epidermal cells and the cellular walls through the stylus thereof, and start feeding from the pericycle cells. Thus, the infested plants become subject to a reduced roots system, rachitis, dwarfism and chlorosis; and due to a reduction in the water absorption the plant may die.

Golden nematode or *Globodera rostochiensis* is a cyst-forming nematode infecting food and ornamental plants, with million dollars loses in a year. This nematode has affected potato-producing zones back from years 70s and from then it has spread to lukewarm and/or mountain zones where said tubercle is grown. Under a conservative appreciation, this nematode produces In Mexico loses for about 800,000 tons of potato production yearly, equivalent to about 3000 million Mexican pesos yearly. In Veracruz state the loses are esteemed in about 50,000 tons of potatoes yearly, equivalent to about 415 million Mexican pesos yearly, since a statistical lowering in the potato production has been observed in Veracruz state (OEIDRUS, 2008).

During 2008 a production of 300 million tons of potato was reported in the world over, with the Republic of China being the main provider and consumer thereof. This food shows a high nutritional value, is a versatile and noble food, has a variety of uses of industrial character, such as starch, maltose, dextrose, molasses and glucose.

According to United Nations' Food and Agriculture Organization (FAO), the world production of potato in 2007 was 325.30 million tons, the main producers being China, Russian Federation, India, United States, Ukraine, Poland, Belarus, Netherlands and France. On the other side, the main consumers of this tubercle are European countries whilst the lower consumers are in Africa and Latin America.

According to the Secretary of Agriculture, Cattle, Rural Development, Fishing and Food (SAGARPA) potato is ranked in Mexico in the 35th place for seeded surface; however, regarding the production value, this tubercle is ranked in the 9th place. More than 8700 producers are dedicated to potato farming in 12 states of the country, the farming of which generates 17,500 direct employments, 51,600 indirect ones and 6.3 million journals every year (2008).

In Veracruz state the mountain zones, such as the slopes of Cofre de Perote and Pico de Orizaba, are the ideal places for growing potatoes. Since 1987 the entire producing zone (6000 Ha) of Veracruz state has been under a quarantine according to the official document "Permanent Interior Quarantine Number 17 against the Potato Golden Nematode *Globodera rostochiensis*", as published in 1987 and in force nowadays, through the Mexican Official Standard NOM040-FITO-2002, wherein requirements and specifications are given for the production and national mobilization of commercial potato, forbidding the use of said tubercle for seeds since this can be a propagator vehicle of nematodes, specifically of *Globodera rostochiensis*. This forbidding has been disrespected thus resulting in a greater dispersion of this noxious plague. These rules show that the problem has remained unsolved for more than 30 agricultural cycles.

Basically, the golden nematode or *Globodera rostochiensis* has affected the Mexican potato-producing zones as back as from about 1972; since it was then when it scattered to the mountain zones where this tubercle is grown. The records of the presence of said parasite show that it reached populations 100 times greater than the recommended value in order to avoid the damage to the production (i.e., 40 cysts per soil kg), according to the European Organization for Plant Protection.

The most commonly employed methods for controlling *Globodera rostochiensis* are the application of nematicides, such as carbofuran, which, further of being toxic, is not a definitive solution. There are in the state of the art methods for controlling nematodes of the *Globodera* spp. by means of the use of synthetic proteins (WO 01/94601 A2), the use of 2R,5R-dihydroxymethyl-3R, R-dihydroxypirrolidine (WO/1999/05941; a chemical agent obtained from plants of the Solanaceae family (WO/1999/059414); through the use of proteinase inhibitors (WO/1992/015690); and by the use of *Bacillus thuringiensis* (WO/1993/019604); compositions with one or more essential oils from *Tagetes erecta, Ocimum basilicium* or *Cymbopongon martini*; a carrier and an emulsifier (WO/2007/13222); compositions based on the bark of *Afrostyrax lepidephyllus* (WO/1995/010187), addition of cisterna proteinase (WO/2008/087555) and, specifically for the control of *Globodera rostochiensis*, the use of *Arthrobotrys* sp. (KR20030094540), which is too much sensitive to ambient factors and is inoperable on de-structured soils; chemical agents obtained from Solanaceae (JP3190807); and a chemical agent of the condensed formula $C_{27}H_{30}O_9$ (WO/1993/002083). These control methods, jointly with the strategy of culture rotation, are generally carried out in a disorganized manner and with scarce knowledge on the nematode cycle of life. This and the doses employed, cause pollution and damages to the freatical mantles, pollution of the product and, in some instances, generate resistance on said nematodes and, consequently, making the eradication thereof more difficult.

The genus *Paecilomyces* spp. has being used in the following applications: *Paecilomyces tenuipes* in the control of flying insects in plants (U.S. Pat. No. 7,033,586 B2, US 20030124098 and US 2007 0141032); a composition containing *Paecilomyces lilacinus* used in the control of soil pests (U.S. Pat. No. 7,435,411 B2, CN101418264 and US 20050008619); *Paecilomyces fumosoroseus* or *Paecilomyces javanicus* in the control of under earth thermites (U.S. Pat. No. 7,390,480); *Paecilomyces javanicus*, combined with imidacloprid in the control of sucker insects (CN101502270); *Paecilomyces javanicus* combined with azadirachtin (CN101331880 and CN101331884); *Paecilomyces fumosoroseus* combined with azadirachtin (CN101273728 and WO/1991/011856); a protein obtained from *Paecilomyces farinosus* as an insecticide (WO/2001/000841); and more particularly, in the control of plants parasite nematodes among which there are: *Paecilomyces lilacinus* (U.S. Pat. No. 598,954, Pat No. CN101422168, Pat No. DE102005024783, Pat No. CN101081982 and Pat No. CA2059642); *Paecilomyces fumosoroseus* (U.S. Pat. No. 5,360,607); *Paecilomyces lilacinus* 251, *Paecilomyces lilacinus* 252, *Paecilomyces lilacinus* 253 and *Paecilomyces lilacinus* 254 (U.S. Pat. No. 5,989,543); and *Paecilomyces cicadae* (CN101518265), without any mention to the use of *Paecilomyces carneus* in the control of nematodes in crops.

According to the above discussed, and as a response to a problem of such an important market throughout the world as the potato market, this invention has been developed to provide an optimized method of production of *Paecilomyces carneus*, as well as uses, methods and compositions easy to be applied in the control and/or prevention and/or eradication of nematodes in Solanaceae, and without a negative effect neither on the soil and on the product or the final consumer.

OBJECTS OF THE INVENTION

This novel invention relates to a fungus *Paecilomyces carneus*, in a non-limitative manner, the strain IE-431 of fungus *Paecilomyces carneus*; methods for producing and spreading the same, and the use thereof as a nematicide on Solanaceae plants for the control of nematodes of the Heteroderidae family, in a non-limitative manner, *Globodera rostochiensis*.

Additionally, compositions and methods are described for the control and/or prevention and/or eradication of nematodes in Solanaceae in order to avoid the damage caused on the crop, characterized by the effect thereof starting from the first culture cycle (which is surprising and non-reported in the state of the art) and without affecting the end quality of the product, but improving the biological and chemical characteristics of the soil.

BRIEF DESCRIPTION OF THE DRAWINGS

FIG. 1. A comparative study of the effect of *Paecilomyces carneus* and *Paecilomyces lilacinus* on *Globodera rostochiensis*.

FIG. 2. A microphotography of strain IE-431 of *Paecilomyces carneus*.

FIG. 3. A microphotography of *Globodera rostochiensis*.

FIG. 4. *Globodera rostochiensis* cysts.

FIG. 5. J2 of *Globodera rostochiensis* infected with *Paecilomyces carneus* strain IE-431, inside the egg.

DETAILED DESCRIPTION OF THE INVENTION

This novel invention disclosed herein below comprises uses, methods and biological compositions of *Paecilomyces carneus* for the control and/or prevention and/or eradication of plant parasites in Solanaceae cultures.

*Paecilomyces carneus* strain IE-431 is a fungus produced according to the methods of this invention. Said strain is presently maintained and registered in the fungal collection of the Instituto de Ecologia (INECOL), and is registered with the World Federation Culture Collection (WFCC) under No. IEWDCM782. The isolation and/or maintain of the *Paecilomyces carneus* strain IE-431 are carried out in one or more solid culture means, constituted by at least a nitrogen source and/or at least a carbon source and/or one or more mineral salts and/or at least a suitable vehicle and/or at least an antibiotic agent and/or at least a growing helper agent. Said culture is incubated within a temperature within the range of from 12° C. to 35° C. for a time enough to obtain a pertinent concentration.

The massive reproduction of the fungus consists in the inoculation of living cells of *Paecilomyces carneus* in liquid media comprising one or more amino acids and/or one or more carbohydrates and/or one or more mineral salts and/or at least one suitable vehicle and/or at least an antibiotic agent and/or at least a growing helper agent. Said culture is incubated at a temperature within a range of from 12° C. to 35° C. for a time enough to obtain a pertinent concentration (FIG. 3).

Said fungus *Paecilomyces carneus* strain IE-431—obtained from a novel process of isolation and/or maintain and/or massive reproduction disclosed in this novel investigation—, exhibits a series of genetic characteristics that are conserved without representative structural changes, which make it different from any other species of *Paecilomyces* and never observed before with any other species belonging to genus *Paecilomyces* spp., characterized in that presents a colony diameter of from 15 to 21 mm in 10 days on agar-oats (AA) media, of from 15 to 19 mm on Agar-dextrose-potato (PDA), while on Agar-carrot-potato (PZA) it grows from 15 to 17 mm. The mycelium thereof is of white to hyaline color (1A1) in the color chart of Farver and Faver of Wanscher and Kornerup (1961); it does not stain the culture media tested both on the front and reverse of the agar plate. The texture thereof is filamentous accented on PZA; it grows very close to the surface of the media (sparse) and becomes dusty when sporulates. Said mycelium deforms the PDA with the appearance of notorious grooves at the reverse of the box. It is shaped as erect, macronematous, simple conidiophores, with no branches with catenulated equinulated conidia of subglobe shape, and some of them have ends slightly pointed at the ends, dimensioned to 2.4-4 µm×2-3.2 µm.

In the solid culture medium, 86% of the conidia germinate at 16 hours, the germ tube varies between 6 and 54 micrometers in length. At 24 hrs 100% of the spores germinate and the mycelium is greater than 30 and less than 110 micrometers in length.

Under the light of the above discussed technical knowledge developed for this invention, we are filing the DNA nucleotide sequence coding *Paecilomyces carneus* strain IE-431, as disclosed at the end hereof.

In this novel investigation, it was surprisingly found that, when living cells of *Paecilomyces carneus* IE-431 were placed in contact with cysts of the nematode *Globodera rostochiensis*, substantial damages were produced on the cysts, such that the propagation of this parasite is avoided. During our investigations, we found that the interaction between *Paecilomyces carneus* and *Globodera rostochiensis* occurs through the fungus germination which, when contacts the cysts (FIG. 4) said cysts are colonized by the mycelium at the interior thereof (FIG. 5) thus surprisingly affecting the whole amount of eggs and larvae J1 and J2 contained within said cyst. The cyst infection starts through an enzymatic process when *Paecilomyces carneus* permeates the cyst wall and then the mycelium grows on the surface of the eggs and the interior of juvenile J1 and J2; therefore, the development of said mycelium becomes invasive to the point of completely degrade the eggs and/or juveniles J1 and J2.

During the investigation a study was carried out on the nematicide effect of *Paecilomyces carneus* strain IE-431 against the effect of *Paecilomyces lilacinus* IE-430 on the *Globodera rostochiensis* cysts, and It was surprisingly found that *Paecilomyces carneus* IE-431 acts in a more rapid and noxious manner against the cysts of said nematode; i.e., there is a significant difference between to pathogenicity of one species and the other against said nematode. This study was carried to laboratory level, evaluating the degree of infection of said cysts with a concentration of living cells of either fungus of $1\times10^6$ living cells/mL, and a third control group with the only addition of distilled sterile water. Said pathogenicity was evaluated for a period of 14 days, according to the macroscopic and microscopic aspects of cysts, and a significant unexpected difference was obtained relating the effect of fungus *Paecilomyces carneus* strain IE-431, compared to *Paecilomyces lilacinus*. Results are shown in FIG. 5.

The next test stage of the use of fungus *Paecilomyces carneus* strain IE-431 as a nematicide was applied singly (TP) and jointly with lima bean (HP) and peas (ChP) crops rotation, with an absolute witness (TA) where neither control nor crop were applied. Said lima bean and peas crops with no treatment with said fungus, are considered as witnesses (H) and (Ch). When the population density is above 200 cysts/100 g of soil (viability average 10-40 and up to 100 eggs/g soil) the first application is effected before seeding; a second application is made during the seeding and a third application is carried out after the harvest of lima bean and peas in order to provide for a decreasing in the golden nematode population down to practically zero (Table 1 and Table 2).

TABLE 1

Effect of *Paecilomyces carneus* on the control of the potato golden nematode, compared to the lima bean crop in rotation and non-farmed plots of land.

| | | Treatments | | | |
|---|---|---|---|---|---|
| parameters | Monitoring | H | HP | TP | TA |
| Cysts 100 g | 1 | 227 | 272 | 171 | 180 |
| | 2 | 155 | 144 | 200 | 189 |
| | 3 | 140 | 102 | 154 | 183 |
| | 4 | 133 | 101 | 153 | 211 |
| Viability 1 g | 1 | 40 | 64 | 13 | 15 |
| | 2 | 14 | 14 | 20 | 13 |
| | 3 | 12 | 7 | 11 | 14 |
| | 4 | 15 | 5 | 9 | 15 |
| J2-Gr 100 g | 1 | 4 | 14 | 3 | 4 |
| | 2 | 7 | 9 | 4 | 3 |
| | 3 | 21 | 6 | 12 | 16 |
| | 4 | 17 | 2 | 3 | 20 |
| Free-living 100 g | 1 | 62 | 131 | 119 | 124 |
| | 2 | 148 | 137 | 78 | 70 |
| | 3 | 72 | 82 | 61 | 52 |
| | 4 | 42 | 72 | 57 | 43 |

TABLE 2

Effect of *Paecilomyces carneus* on the control of the potato golden nematode, compared to the peas crop in rotation and non-farmed plots of land.

| | | Treatments | | | |
|---|---|---|---|---|---|
| parameters | Monitoring | cH | chP | TP | TAC |
| Cysts 100 g | 1 | 151 | 173 | 250 | 237 |
| | 2 | 139 | 134 | 139 | 109 |
| | 3 | 146 | 95 | 126 | 130 |
| | 4 | 128 | 118 | 124 | 99 |
| Viability 1 g | 1 | 24 | 19 | 17 | 26 |
| | 2 | 17 | 19 | 15 | 19 |
| | 3 | 15 | 13 | 14 | 15 |
| | 4 | 8 | 7 | 9 | 10 |
| J2-Gr 100 g | 1 | 5 | 3 | 11 | 10 |
| | 2 | 1 | 3 | 11 | 8 |
| | 3 | 9.8 | 13 | 8 | 18 |
| | 4 | 6 | 8 | 4 | 16 |
| Free-living 100 g | 1 | 73 | 105 | 84 | 70 |
| | 2 | 73 | 101 | 80 | 69 |
| | 3 | 61 | 55 | 69 | 72 |
| | 4 | 62 | 56 | 115 | 50 |

As can be seen from the above, *Paecilomyces carneus* strain IE-341 has a nematicide effect on the viability of the potato golden nematode cysts but no action on free life nematodes, which are to be kept on farming soils. Under this investigation, we found a synergic behavior for reducing the population density of golden nematode when the application of *Paecilomyces carneus* is combined with the rotation of cultures that are not favorable to the bursting of J2 *Globodera rostochiensis*.

It is to be said that the use of rotation with lima bean and peas without the application of *Paecilomyces carneus* as a bionematicide is also effective, but requires of a period of time greater than 4 years.

Following an exhaustive investigation, a method is provided for isolation, maintaining, massive reproduction of *Paecilomyces carneus* strain IE-431, as well as the use thereof in the control and/or prevention and/or eradication of cyst-forming nematodes or having characteristics similar to *Globodera rostochiensis* on cultures of the Solanaceae family, such as potato, chili, tomato, eggplant, among other plants where this type of parasite grows, such as *Avena sativa* and *Vicia villosa* (Winter Veza), and tobacco.

Further to the products of this invention, nematicide compositions are provided comprising living cells of *Paecilomyces carneus* strain IE-431 and at least a living cells carrier and optionally a device for the application of said nematicide. The composition preferred for application to farmings is in a suspension shape; however, these compositions can be developed and applied in the shape of pellets, powder, capsules, emulsion, microemulsion, solution or any other form of application existing in the state of the art.

EXAMPLES

Herein below, intended to be descriptive rather than restrictive, are provided compositions employed for the propagation of fungus *Paecilomyces carneus* strain IE-431 and the nematicide compositions obtained.

Example 1: Composition A for Mass Propagation of *Paecilomyces Carneus* Strain IE-431

| INGREDIENT | AMOUNT |
|---|---|
| Carrot juice | 80-100 mL |
| Ampicilina | 500 mg |
| Water | q.s. 1000 mL |

Example 2: Composition B for Mass Propagation of *Paecilomyces Carneus* Strain EI-431

| INGREDIENT | AMOUNT |
|---|---|
| Oats | 20-50 gL |
| yeast | 0.1-5.0 g/l |
| Carrot juice | 50-150 mL7L |
| Chloramphenicol | 1000 mg |
| Water | q.s. 1000 mL |

Example 3: Composition C for Isolation and Maintain of *Paecilomyces Carneus* Strain IE-431

| INGREDIENT | AMOUNT |
|---|---|
| Carrot | 50-160 g/L |
| Oats | 20-50 g/L |
| Chloramphenicol | 1000 mg |
| Water | c.b.p. 1000 mL |

Example 4: Nematicide Composition A-1

| INGREDIENT | AMOUNT |
|---|---|
| Living cells of *P. carneus* | $0.5 \times 10^7$/mL |
| Composition A | 1000 mL |

Example 5: Nematicide Composition B1

| INGREDIENT | AMOUNT |
|---|---|
| Living cells of *P. carneus* | $3 \times 10^7$/mL |
| Composition B | 1000 mL |

Example 6: Nematicide Composition C-1

| INGREDIENT | AMOUNT |
|---|---|
| Living cells of *P. carneus* | $0.3 \times 10^7$/mL |
| Composition C | 1000 mL |

In an integral manner, this invention provides the following advantages:

1.—A method of agricultural control, based on clean and supporting technologies.

2.—Said method produces an improvement on the soil quality since allows for the recovery of soils used in Solanaceae cultures.

3.—The time to eradicate nematodes is one cycle, whereby it may stop the permanent interior quarantine number 17 against the potato golden nematode *Globodera rostochiensis*.

4.—An immediate improvement is produced on the quality of the obtained product, enlarging the shelf life thereof.

5.—The nematicide compositions obtained are innocuous for both humans and animals.

6.—The population of the golden nematode is reduced from the very first application.

7.—The cysts are directly attacked whereby better agricultural products are obtained from the very first application.

8.—It can be combined with other control methods, such as rotation.

The invention claimed is:

1. A method of controlling or eradicating nematodes in a culture parasited by a cyst-forming nematode, comprising applying a composition comprising: *Paecilomyces carneus* fungus;
   either ampicillin or chloramphenicol;
   oats, carrot juice, and water
to the culture.

2. The method of claim 1, in which the culture is a Solanaceae culture.

3. The method of claim 1, in which the *Paecilomyces carneus* fungus is applied to the culture in combination with at least one carrier.

4. The method of claim 1, in which the *Paecilomyces carneus* fungus is applied to a culture simultaneously with a culture rotation.

5. The method of claim 1, in which the *Paecilomyces carneus* fungus is applied prior to the culture, during the culture and/or after every culture cycle.

6. A bio-nematicide composition for the control, or eradication of nematodes comprising:
   a living cell suspension of a *Paecilomyces carneus* fungus;
   either ampicillin or chloramphenicol;
   oats, carrot juice, and water.

7. The method of claim 1, in which nematode is a *Globodera* spp.

8. The method of claim 1, in which a living cell suspension of a *Paecilomyces carneus* fungus is applied combined with at least one carrier.

9. The composition of claim 6, in which the composition comprises chloramphenicol.

10. The composition of claim 6, wherein the composition comprises 500-1000 mg of ampicillin or chloramphenicol, 50-150 ml/l of carrot juice, 20-50 g/l of oats, and 0.5-5 g/l of yeast.

* * * * *